United States Patent [19]

Cachier

[11] 4,152,718
[45] May 1, 1979

[54] SEMICONDUCTOR STRUCTURE FOR MILLIMETER WAVES

[75] Inventor: Gérard Cachier, Paris, France

[73] Assignee: Thomson-CSF, Paris, France

[21] Appl. No.: 792,735

[22] Filed: May 2, 1977

[30] Foreign Application Priority Data

May 11, 1976 [FR] France ............................ 76 14164

[51] Int. Cl.² ..................... H01L 29/06; H01L 23/48; H01L 29/46
[52] U.S. Cl. ...................................... 357/56; 357/55; 357/75; 357/71; 357/72; 357/81
[58] Field of Search ...................... 357/55, 56, 75, 76, 357/71, 72, 81

[56] References Cited

U.S. PATENT DOCUMENTS

| 3,447,057 | 5/1969 | Brown et al. | 357/75 |
| 3,699,402 | 10/1972 | McCann et al. | 357/76 |
| 3,867,666 | 2/1975 | Nyul | 357/56 |
| 3,896,473 | 7/1975 | DiLorenzo | 357/56 |
| 3,896,478 | 7/1975 | Henry | 357/55 |
| 4,047,197 | 9/1977 | Schierz | 357/75 |

FOREIGN PATENT DOCUMENTS 2216424  10/1972  Fed. Rep. of Germany ............ 357/56

Primary Examiner—Andrew J. James
Attorney, Agent, or Firm—Edwin E. Greigg

[57] ABSTRACT

A method for manufacturing semiconductor devices and the devices so made, having two components with differing internal structures of very small dimension on a common heat-dissipating support, wherein the two components are obtained by suitable ion implants in two separate regions of a single block of silicon by alternately protecting each region with a mask. After welding the structure to a metallic support, a pair of diodes or mounds is relieved by ion machining or chemical etching. The assembly is then insulated and provided with the necessary power connections by the alternate application of insulating and conductive materials, the latter being separate metallic layers enabling the two components to be discretely biased.

5 Claims, 8 Drawing Figures

SEMICONDUCTOR STRUCTURE FOR MILLIMETER WAVES

BACKGROUND OF THE INVENTION

This invention relates to an improved method for making a circuit for millimetric waves comprising a semiconductive diode and another semiconductive component. The invention also relates to the structures produced by this method.

There are already methods for making unitary structures comprising a circuit for millimetric waves embedded in an integrating block, an impedance matching circuit, and heat dissipating means.

Structures of this type comprise, for example, an avalanche diode welded to a metallic support and surrounded by a dielectric ring, the central orifice of the ring being filled with a resin having the same dielectric coefficient as the ring, the assembly being lapped and then plated with a metallic layer which protects the assembly and forms a feed terminal, while the metallic support acts as a heat dissipator and electrical ground.

In many cases, the circuit is part of a more complex assembly, such as an oscillator tunable by a variable-capacity diode or an oscillator associated with a mixer diode. This additional diode gives rise to the same problems of protection and contacting as had been solved for the actual source.

OBJECTS AND SUMMARY OF THE INVENTION

An object of the present invention is to enable the above-mentioned problems to be solved.

Another object of the invention is to integrate into the same semiconductor device two components with different internal structures having very small dimensions on a common heat-dissipating support.

These objects will be achieved by the method according to the invention which in summary comprises the following steps:

first step: A block of semiconductor material is provided with two planar, opposed major surfaces, the first surface having a substrate adjacent thereto, and the secondary surface having semiconductive layers parallel with and adjacent thereto, to which block there is welded a metallic support on a side of the second surface adjacent said semiconductive layers;

second step: then the substrate is lapped and the semiconductive block is cut by ion machining or chemical etching into two mounds, each having different structures;

third step: then the assembly obtained in the second step is finished by successively depositing insulating and conductive materials, separate metallic layers being applied to the diode and to said semi-conductive component.

The invention will be better understood as well as further objects and advantages thereof become more apparent from the ensuing detailed description taken in conjunction with the drawing.

DESCRIPTION OF THE PREFERRED EMBODIMENT

Figure 1:
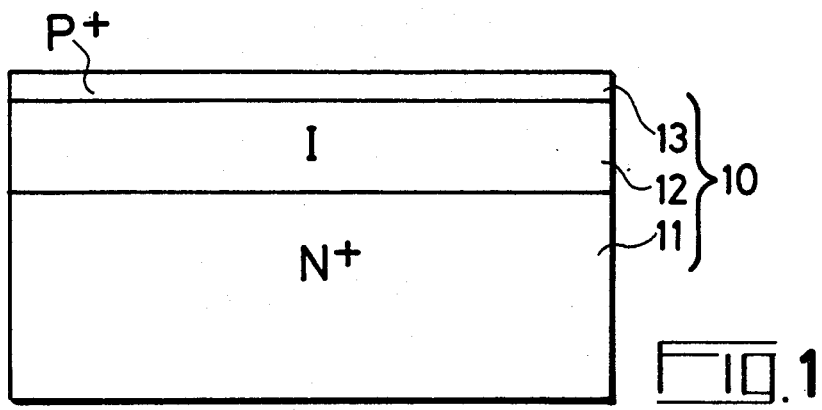
FIGS. 1, 2 and 3 illustrate, with reference to the preferred embodiment, the starting point and two successive stages of a preliminary step of the method.

In the preferred embodiment, there is provided a block 10 (FIG.1) of monocrystalline silicon comprising a heavily doped ($N^+$-type) parallelepipedic substrate 11 having two major surfaces. A first layer 12 of quasiintrinsic monocrystalline silicon and a second layer 13 of heavily doped ($P^+$-type) silicon have been deposited by successive epitaxial processes to the first major surface.

Figure 2:
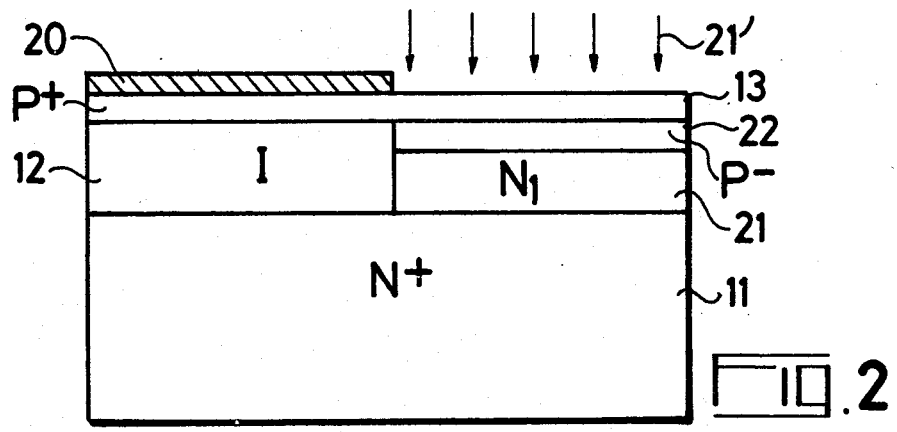

Preliminary step: to the block illustrated in FIG. 2, a screen 20 is placed on a portion of the layer 13, for example, in such a manner as to protect half of the silicon layer 13. This screen is formed, for example, by the deposit of a thin metallic layer upon layer 13 in a vacuum evaporator. In this operation, half the surface is protected by preliminary masking with resin, thus obtained by deposit of a photosensitive resin, partial exposure and photographic development. Layer 13 is then subjected to two successive ion implants by beams of radiation 21', each exposure implanting different ions (phosphorus and boron, for example), and thus making it possible to obtain, by suitably selecting the energy and density levels:

a layer 21 with N-type conductivity and a doping level $N_1$ whose depth is a major portion of the layer 12, and whose extent is substantially defined by the unprotected portion thereof;

a layer 22 with P-type conductivity (weakly doped), whose depth is the remainder of the layer 12.

An avalanche diode structure, for example, is obtained by the preceding preliminary step of the method.

Figure 3:
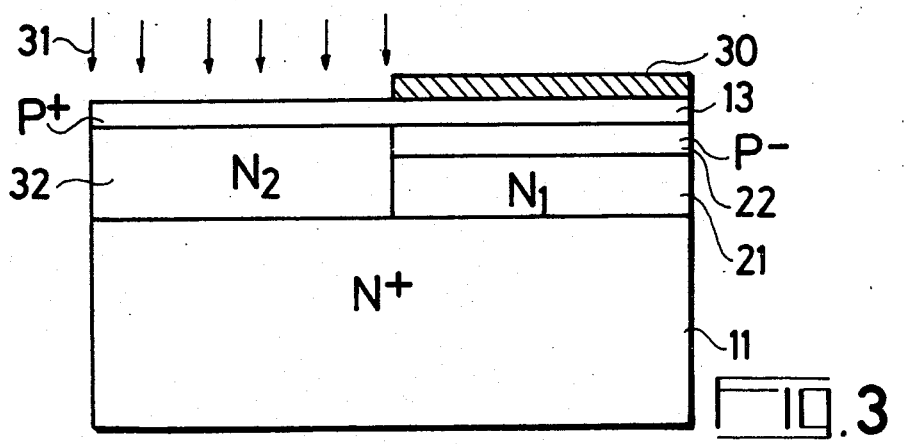

FIG. 3 shows the result of an ion implant operation by means of radiation exposure 31 to the previously protected layer 12 carried out by a method similar to that which has just been described with reference to FIG. 2. In this case, a protection screen 30 protects the layers 21 and 22. The ion implant operation produces a layer 32 having a doping level $N_2$. The resultant device is, for example, a variable-capacity diode.

Figure 4:
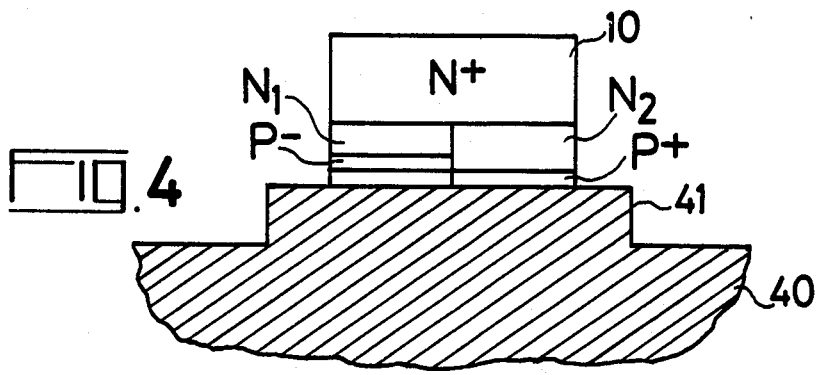
FIG. 4 illustrates the first step of the method of this invention applied to the embodiment of FIGS. 1-3.

First step: (FIG. 4) The block 10 of semiconductive material is then inverted and welded to a cylindrical projection 41 of a metallic support 40, comprising, for example, gold-plated copper. The $p^+$-layer is brought into contact with said support, for example, during a thermocompression process.

Figure 5A:
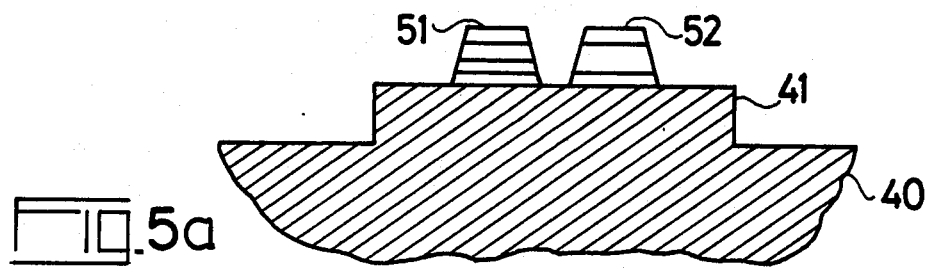
FIG. 5 includes a sectional view (a) and an elevational view (b) illustrating the result of the second step in the same embodiment.
Figure 5B:
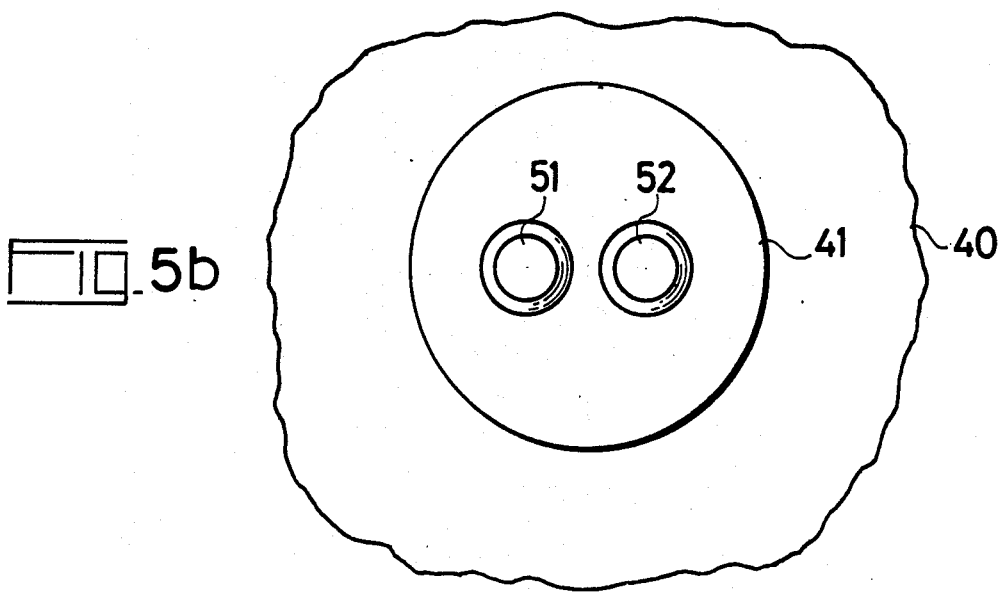

Second step: the $N^+$-substrate layer 10 left free during the welding operation carried out in the preceding step, is then subjected to a lapping operation which is facilitated by the metallic support which serves as a bracing means. The block 10 is then subjected to ion machining to form two substantially cylindrical regions comprising respectively part of the layer $N_1$ and part of the layer $N_2$. There are thus obtained two independent structures 51 and 52 (FIG. 5), mounted on the same metallic support. If the diameter of the projection 41 is 300 microns, for example, the two diodes 51 and 52 each are machined to have a mean diameter of the order of 50 microns with a height of approximately 10 microns. With dimensions such as these, the individual welding of these diodes would be extremely difficult if the method according to the invention were not available.

Figure 6:
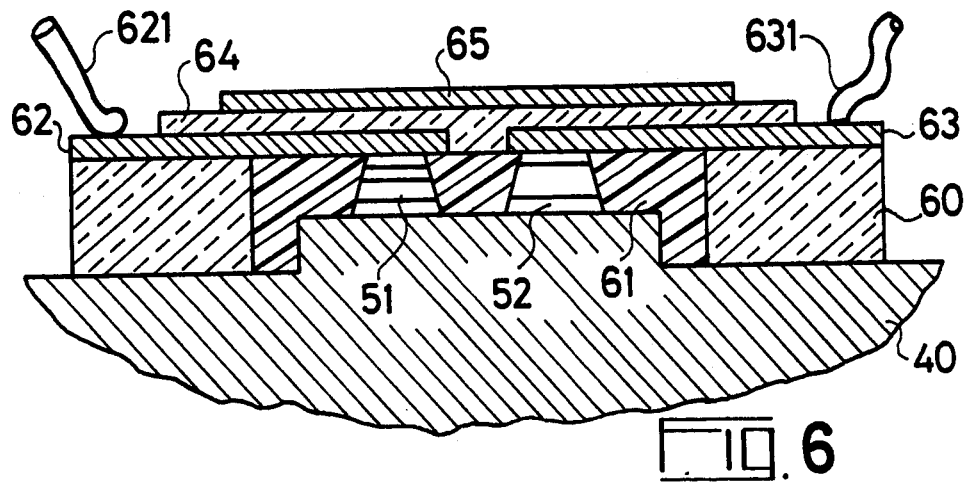
FIG. 6 shows the article obtained after the third step in the same embodiment.

Third step: FIG. 6 illustrates the resultant structure obtained upon completion of the following operations:

(a) bonding a dielectric ring 60, for example, quartz-type glass, to the metallic support 40, said ring being provided with a diameter slightly greater than that of the central projection of the support 40. The ring has been previously lapped so that its height places its upper surface coplanar with the level of the upper surfaces of the diodes 51 and 52.

(b) Filling the inner part of the ring with a resin 61 having a dielectric constant of the same order as that of the glass, for example, polyamide resin.

(c) After lapping to expose the upper surfaces of the diodes, successive deposits of titanium and gold are applied by evaporation on the upper surface of the structure to form two metallic layers 62 and 63, respectively. FIG. 6 shows these layers to be clearly separated from one another in the zone situated between the two diodes. Only one thickness of deposit is shown, however, the layer of titanium is considerably thinner than the layer of gold.

(d) After masking peripheral zones of layers 62 and 63, a layer of dielectric is deposited, for example, by cathode sputtering of silica to form a layer 64 thereupon.

(e) Plating the upper surface of layer 64 by deposit of a layer of gold 65, but leaving a peripheral margin to prevent short-circuiting of the metallic layers 62 and 63.

(f) Welding connecting wires 621 and 631 to the metallic layers 62 and 63, respectively, in the peripheral margins left after the preceding steps.

In regard to the operation, it can be seen that the two diodes are separately supplied with direct current, and they may be jointly supplied with high frequency, through the layer 64 of silica, by means of the metallic layer 65 with mechanical contact.

In a variant of this embodiment, the operations (d) and (e) of step three may be eliminated and high frequency supplied by one of the connecting wires 621 and 631, provided that the mutual capacity of the adjacent metallic layers 62 and 63 is sufficient to ensure effective coupling.

Figure 7:
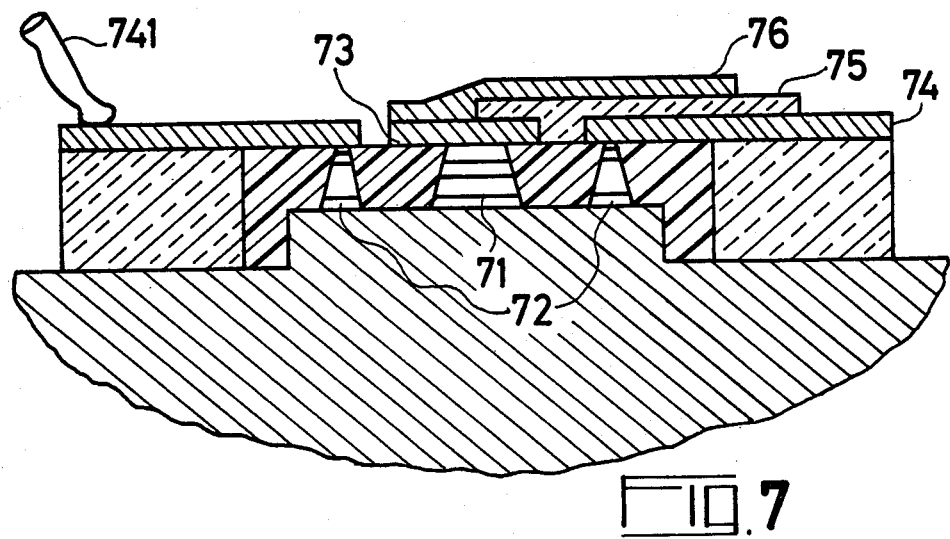
FIG. 7 is a diagramatic sectional view of a structure obtained by the application of the method to a second embodiment.

FIG. 7 shows another embodiment of the invention by which it is possible to obtain a diode 71 at the center of the structure and in concentric spaced relation thereto, an annular diode 72.

In order to obtain this result, the screens 20 and 30 illustrated in FIGS. 2 and 3 are placed by successive use of varying-diameter circular screens.

The operations carried out in the various steps of the first embodiment are used, except for the following differences in the third step:

in operation (c), two concentric metallic layers 73 (centrally disposed) and 74 (peripherally disposed) are deposited, the peripherally disposed metallic layer being intended to cooperate with the annular diode;

in operation (d), a layer of silica 75 is deposited assymmetrically upon metallic layers 73 and 74 so that at least part of the centrally disposed metallic layer 73 is left revealed;

in operation (e), there is deposited a metallic layer 76 which is welded to the part of the metallic layer 73 left revealed;

in operation (f), a connecting wire 741 is welded to the metallic layer 74 to feed the annular diode, while the central diode is fed by mechanical contact with the final metallic layer 76. The two feeds are used both for direct current and for high frequency.

The invention is applicable to any device manufacturable by the method described above and, in particular, to millimetric wave oscillators associated with a variable-capacity diode or with a mixer diode.

The semiconductive material may be silicon, gallium arsenide or any other semiconductive material capable of use at very high frequencies.

What is claimed is:

1. A semiconductor device for use in a millimetric wave circuit comprising, in combination, a heat dissipating support, a pair of mounds each formed of layers of semiconductive material disposed on said support in spaced-apart relationship, and pair of mounds having different internal structures so as to provide differing functions, a dielectric ring having a central opening disposed on said support in encircling relationship with said pair of mounds to define an annular channel, said channel being filled with a resin whose dielectric constant equals that of said ring, said resin and said mounds being provided with a coplanar upper surface, a pair of coplanar metallic layers on said coplanar upper surface, each of said metallic layers being connected to a respective one of said pair of mounds, a layer of dielectric material on at least a portion of said pair of metallic layers such that at least one extremity of each of said pair of metallic layers is exposed to provide for welding conductive wires thereto and a metallic layer on said layer of dielectric material.

2. A semiconductor device as defined in claim 1, wherein said pair of mounds are disposed to form a space filled by said resin, and wherein said coplanar metallic layers form a space filled by said dielectric material for contacting said resin.

3. A semiconductor device as defined in claim 1, wherein one of said mounds is annular and concentric with the other mound defining therewith another annular channel filled by said resin, wherein one of said pair of coplanar metallic layers engages the other mound and the other of said coplanar metallic layers engages the annular mound, wherein said coplanar metallic layers form a space filled by said dielectric material for contacting the resin in said another annular channel, and wherein said metallic layer engages one of the coplanar metallic layers.

4. The semiconductor device as defined in claim 1, wherein one of said mounds defines an avalanche diode and the other of said mounds defines a variable-capacity diode.

5. The semiconductor device as defined in claim 1, wherein one of said mounds defines an avalanche diode and the other of said mounds defines a mixer diode.

* * * * *